US011173438B2

(12) United States Patent
Rodriguez et al.

(10) Patent No.: US 11,173,438 B2
(45) Date of Patent: Nov. 16, 2021

(54) FILTER HAVING TRACER MATERIAL

(71) Applicant: Caterpillar Inc., Deerfield, IL (US)

(72) Inventors: Javier A. Rodriguez, Peoria, IL (US); Philip C. Spengler, Washington, IL (US); Darrell L. Morehouse, III, Dunlap, IL (US); Hind M. Abi-Akar, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 372 days.

(21) Appl. No.: 16/131,736

(22) Filed: Sep. 14, 2018

(65) Prior Publication Data

US 2020/0086254 A1 Mar. 19, 2020

(51) Int. Cl.
| *B01D 29/11* | (2006.01) |
| *B01D 35/00* | (2006.01) |
| *B01D 35/143* | (2006.01) |
| *B01D 37/02* | (2006.01) |
| *B33Y 80/00* | (2015.01) |
| *G01N 33/28* | (2006.01) |

(52) U.S. Cl.
CPC .......... *B01D 37/025* (2013.01); *B01D 29/111* (2013.01); *B01D 29/114* (2013.01); *B01D 35/005* (2013.01); *B01D 35/143* (2013.01); *B33Y 80/00* (2014.12); *G01N 33/2882* (2013.01); *B01D 2201/302* (2013.01); *B01D 2239/04* (2013.01)

(58) Field of Classification Search
CPC ... B01D 29/111; B01D 29/114; B01D 35/005; B01D 35/143; B01D 37/025; B01D 2201/302; B01D 2239/04; B33Y 80/00; G01N 33/2882
See application file for complete search history.

(56) References Cited

U.S. PATENT DOCUMENTS

| 8,425,772 | B2 | 4/2013 | Martin et al. |
| 9,422,793 | B2 | 8/2016 | Gomes et al. |
| 2005/0173325 | A1* | 8/2005 | Klein .................... C10M 137/10 210/209 |
| 2005/0194312 | A1 | 9/2005 | Niemeyer et al. |
| 2007/0193935 | A1* | 8/2007 | Elsenbaumer ....... B01D 37/025 210/209 |
| 2011/0278215 | A1* | 11/2011 | Martin ................. B01D 37/025 210/209 |
| 2014/0034564 | A1 | 2/2014 | Jeung et al. |
| 2014/0230224 | A1 | 8/2014 | Unger et al. |
| 2018/0001236 | A1 | 1/2018 | Marchione et al. |
| 2018/0172661 | A1* | 6/2018 | Spengler ............ G01N 21/3577 |

FOREIGN PATENT DOCUMENTS

| CN | 105041529 A | 11/2015 |
| DE | 10 2013 014 688 A1 | 3/2015 |
| JP | H11 28318 A | 2/1999 |
| WO | WO 2018/112233 A1 | 6/2018 |

OTHER PUBLICATIONS

Search Report and Written Opinion in International Application No. PCT/US2019/050327, dated Dec. 3, 2019.

* cited by examiner

*Primary Examiner* — Lucas A Stelling
(74) *Attorney, Agent, or Firm* — Bookoff McAndrews PLLC

(57) ABSTRACT

An oil filter may include a housing. The housing may include an inlet, an outlet, and a filter element. The filter element may be located downstream of the inlet and upstream of the outlet. Additionally, the filter element may include a filtering material and a tracer material.

20 Claims, 4 Drawing Sheets

FILTER HAVING TRACER MATERIAL

TECHNICAL FIELD

The present disclosure relates generally to filters, and more particularly, to filters having tracer material.

BACKGROUND

Fluid filters are often used in vehicles and heavy equipment, for example, construction and mining equipment, to remove contaminants from working fluids that help power, lubricate, drive, and/or control the mechanisms and engines of the equipment. Over time, contaminants collect in the fluids that may be detrimental to the components using the fluid. Fluid filters help remove the contaminants in the fluids to prolong the useful life of the components. Fluid filters may include a housing and a filter element within the housing, and the filter element may include a permeable filter media made of a filtering material. Due to wear and contaminant accumulation, the filter elements may need to be replaced periodically. In the case of oil filters, it may be difficult to determine when the last service of the oil filter was performed (i.e., when the oil filter was last replaced). Further, it may be difficult to determine if a customer/user has been using oil filters of a specific brand.

An exemplary fluid filter is disclosed in U.S. Pat. No. 8,425,772 issued to Martin et al. on Apr. 23, 2014 ("the '772 patent"). The '772 patent describes a filtration device that includes a filter component and an additive component. The filter component of the '772 patent includes concentrically arranged filtering elements disposed in a filter-in-filter configuration. The additive component includes at least one additive material that is introduced into a working fluid to be filtered. The additive material can be incorporated in the filter component or disposed external to the filter component. For example, the additive material can be soaked in the filter media, coated onto the filter media, added as a layer to the filter media, or otherwise put in the filtering element. The additive material is defined as a chemical material that may be introduced to a working fluid for treating or enhancing the working fluid. The '772 patent lists several examples of additive materials such as lubricity enhancing agents, dispersants, detergents, cetane improvers, flow improvers, fuel burning catalysts, corrosion inhibitors, deicers, pour point suppressants, antioxidants, conductivity improvers, and microbicides. However, the filtration device of the '772 patent does not disclose using tracers in the filter component to assist in indicating a usage of the filter, and/or an origin of the filter. The filter element of the present disclosure may solve one or more of the problems set forth above and/or other problems in the art. The scope of the current disclosure, however, is defined by the attached claims, and not by the ability to solve any specific problem.

SUMMARY

In one aspect, an oil filter may comprise: a housing including: an inlet; an outlet; and a filter element located downstream of the inlet and upstream of the outlet, the filter element including: a filtering material; and a tracer material.

In another aspect, a filter element for a liquid filter may comprise: a filtering material; and a tracer material within the filtering material.

In yet another aspect, a liquid filter may comprise: a filter element including: a filtering material formed by an additive manufacturing process and configured to allow liquid to pass through the filter element such that contaminants are removed from the liquid; and a tracer material added to the filter element by the additive manufacturing process, the tracer material configured to dissolve into the liquid as the liquid is passed through the filter element to provide an indication of the amount of liquid that has passed through the filter element.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. For the purpose of this disclosure, the term "fluid" is broadly used to refer to all types of liquids and gases that may be filtered in a machine or equipment (e.g., hydraulic fluid, oil, diesel, gasoline, air, etc.). Moreover, relative terms, such as, for example, "about," "substantially," "generally," and "approximately" are used to indicate a possible variation of ±10% in a stated value.

Figure 1:
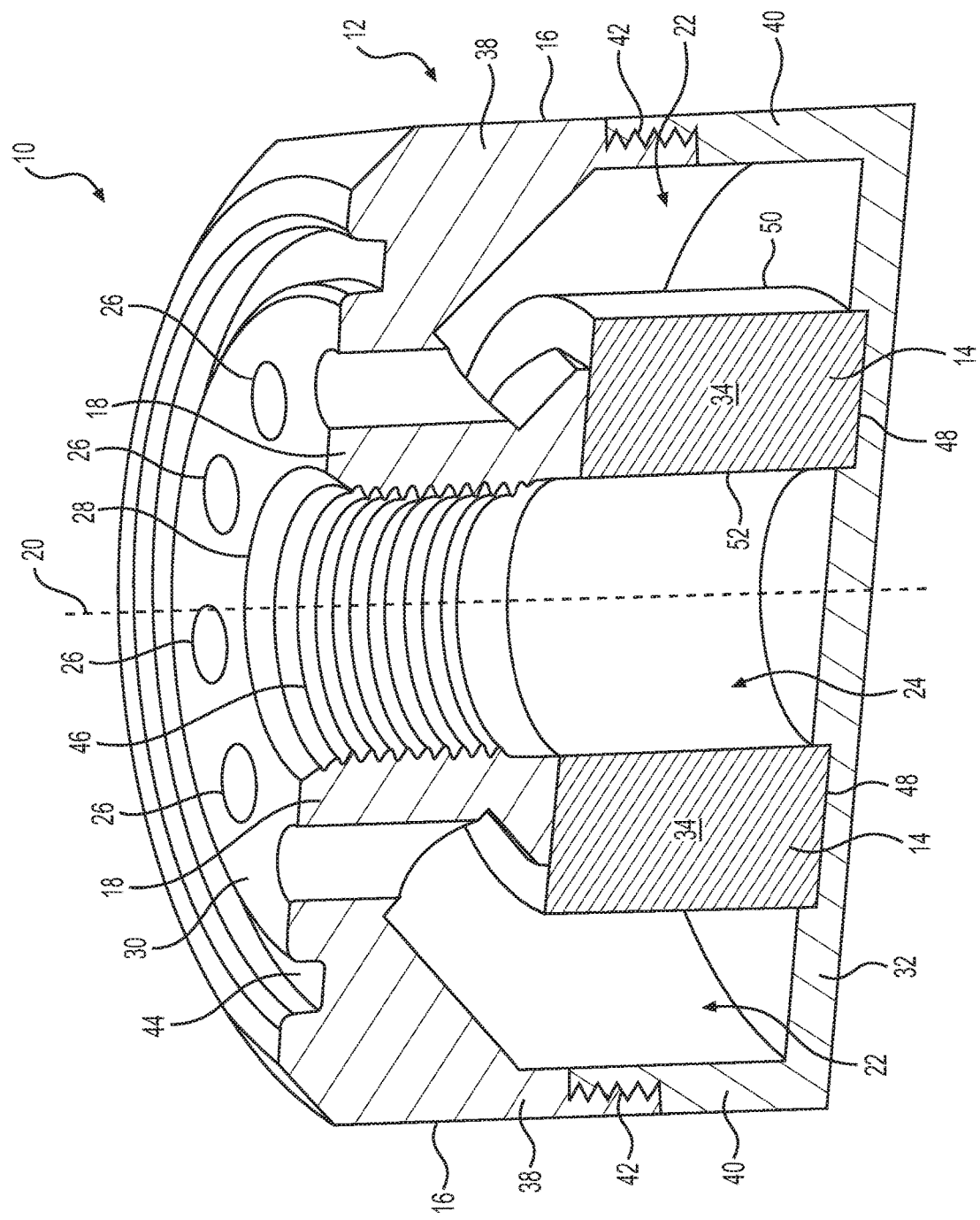
FIG. 1 illustrates a cross-sectional view of a fluid filter, such as an oil filter, according to aspects of this disclosure.

FIG. 1 illustrates a cross-sectional view of a fluid filter, such as oil filter 10, according to aspects of the present disclosure. As used herein, the term oil includes any petroleum-based liquid for use as a working fluid, fuel, and/or lubricant. As shown in FIG. 1, oil filter 10 may include a housing 12 and a filter element 14. Housing 12 may include a longitudinal axis 20 and have an outer radial wall 16 and end walls 18 and 32 at opposite ends of the outer radial wall 16. A filter element 14 may be positioned within the housing 12 between the end walls 18 and 32 to separate an outer cavity 22 and an inner cavity 24 within the housing 12. Housing 12 may further include one or more inlets 26 in fluid communication with the outer cavity 22 and an outlet 28 in fluid communication with the inner cavity. The flow of fluid (e.g., oil) to be filtered may be in a direction such that the filter element 14 is located downstream of the one or more inlets 26 and upstream of the outlet 28. Therefore, filter element 14 may filter fluid as the fluid flows from outer cavity 22 into inner cavity 24.

Housing 12 may include a substantially cylindrical shape. The one or more inlets 26 may include a plurality of cylindrical holes, arranged in a circular array about the longitudinal axis 20. The one or more inlets 26 may extend from a top surface 30 of end wall 18 to outer cavity 22 within housing 12. Likewise, the outlet 28 may extend from the top surface 30 of end wall 18 to inner cavity 24 within housing 12. The number and placement of the one or more inlets 26 and the outlet 28 may be varied as needed or desired in various embodiments. As further shown in FIG. 1, housing 12 may include a top portion 38 and a bottom portion 40. Top portion 38 and bottom portion 40 may each include a threading such that top portion 38 and bottom portion 40 may be coupled at a threaded coupling 42. Top portion 38 and bottom portion 40 may be uncoupled by unscrewing threaded coupling 42 to allow access to the interior of housing 12, for example, to inspect, clean, or replace filter element 14. Top surface 30 may include one or more grooves 44 surrounding the one or more inlets 26. Moreover, outlet 28 may include a threading 46 or other coupling interface in end wall 18. The one or more grooves 44 and/or threading 46 may help couple oil filter 10 to a fluid system. Additionally, bottom portion 40 may also include a filter slot 48 to receive a portion of filter element 14. Filter slot 48 may be a ring-shaped indentation in an interior surface of end wall 32 of housing 12. Filter slot 48 may help to position and to retain filter element 14 within housing 12. While the structural configuration of filter housing 12 is shown in FIG. 1, the filter housing 12 could include any shape or configuration, including any shape, configuration, or orientation of the filter walls, inlets, outlets, internal cavities, filter element location, etc.

Filter element 14 may be a separate component removably positioned within housing 12, or may be integrally formed with housing 12. Filter element 14 may include a filtering material or filter media 34 formed in a hollow cylindrical, ring, or tubular shape such that filter element 14 may include an annular shape defining an outer annular surface 50 and an inner annular surface 52. The outer annular surface 50 of filter element 14 may be in fluid communication with the outer cavity 22 and the inner annular surface 52 of filter element 14 may be in fluid communication with inner cavity 24. Filter element 14 may include a support structure or frame (not shown) to help support or add rigidity to filter media 34. As used herein, filter element 14 may include only the filter media 34, or the filter element 14 may include the filter media 34 and the support structure or frame (not shown). The filter media 34 may be permeable and may include a filtering material 54, such as a fabric, a layered plastic, a woven material, a non-woven material, or a combination of any of these materials or other filtering materials. As such, filter media 34 may include a plurality of pores (not shown) that may allow for the fluid (e.g., oil) to pass through filter element 14. The plurality of pores may be any suitable size (micron rating) such that contaminants of a particular size are not able to pass through filter element 14, while allowing for an appropriate fluid flow rate through filter element 14. In other embodiments, filter element 14 may be a meshed screen, other porous material, or particle sieves. Although not shown, filter element 14 may also include a plurality of different filter elements provided in a concentric manner to provide multi-staged filtering.

Although housing 12 and filter element 14 are discussed above as being substantially cylindrical, this disclosure is not so limited. For example, housing 12 and filter element 14 may be substantially oval or elliptical, rectangular, pentagonal, hexagonal, octagonal, etc. Additionally, filter slot 48 may be any appropriate shape to correspond to the shape of filter element 14 such that filter slot 48 may receive a portion of filter element 14. As such, filter element 14 may be coupled to housing 12, for example, by positioning filter element 14 within filter slot 48 and against an inner portion of end wall 18. Coupling top portion 38 and bottom portion 40 may help to secure filter element 14 within filter slot 48.

Figure 2B:
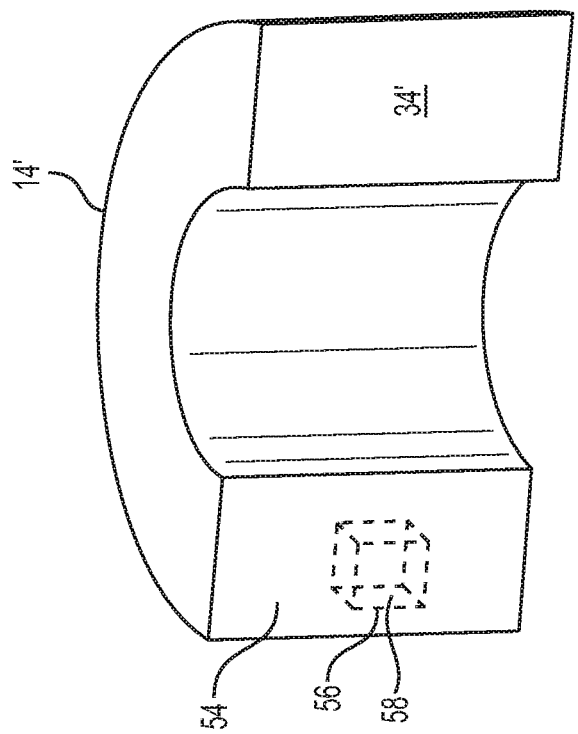
FIG. 2B illustrates a cross-sectional view of an alternative filter element for use in the fluid filter of FIG. 1.
Figure 2A:
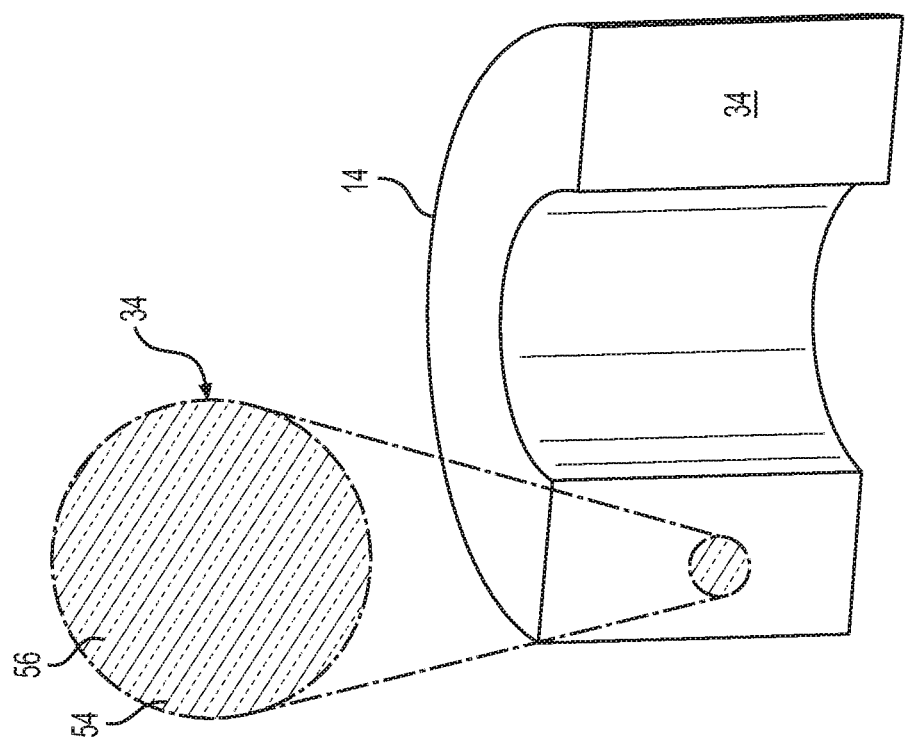
FIG. 2A illustrates a cross-sectional view of a filter element isolated from the fluid filter of FIG. 1, with an enlarged circular cross-sectional view of a portion of the filter element, according to one embodiment.

FIG. 2A illustrates a cross-sectional view of the filter element 14 isolated from the oil filter 10, with an enlarged circular cross-sectional view of a portion of the filter media 34, according to one embodiment. As shown in FIG. 2A, the filter media 34 may include a filtering material 54 and a tracer material 56. In one embodiment, the tracer material 56 may be disposed within and located throughout the filtering material 54 such that the filtering material 54 and the tracer material 56 may constitute a single structure making up the filter media 34. For example, the tracer material 56 may be mixed in with the filtering material 54 during the formation of the filter media 34, such as during an additive manufacturing process, as described below. In other embodiments, the tracer material 56 may be disposed as a layer of material after n-number of layers of filtering material 54, such that the tracer material 56 layer is disposed between layers of filtering material 54. For example, filter media 34 may include at least a first layer of filtering material 54, a second layer of tracer material 56, and a third layer of filtering material 54. This pattern may be repeated until the filter media 34 is fully constructed.

FIG. 2B illustrates a cross-sectional view of a filter element 14' isolated from the oil filter 10, with a cross-sectional view of a tracer element 58 within the filter media 34', according to one embodiment. As shown in FIG. 2B, the filter media 34' may include a filtering material 54 and a tracer element 58 made of tracer material 56. The tracer element 58 may be a substantially solid structure. For example, the tracer element 58 may include a block made of tracer material 56 located within the filtering material 54 of the filter media 34'. In the exemplary embodiment shown in FIG. 2B, the tracer element 58 may be generally cube shaped. However, the tracer element 58 may be any suitable size and shape as necessary. In one embodiment, a single tracer element 58 may be located within the filtering material 54 of the filter media 34'. In other embodiments, a plurality of tracer elements 58 may be located in the filtering material 54 of the filter media 34'. Each of the plurality of tracer elements 58 may be located in various longitudinal, radial, and circumferential locations of the filter element 14. For example, a first tracer element 58 may be located at a first longitudinal, radial, and/or circumferential position and a second tracer element 58 may be located at a second longitudinal, radial, and/or circumferential position.

In the embodiments of FIG. 2A and FIG. 2B, the filtering material 54 may be any suitable material that has a desired structural strength and that is chemically compatible with the fluid to be filtered. When filter element 14 is used for oil, for example, the filtering material 54 may be chemically compatible with hydrocarbons. In one embodiment, the filtering material 54 may be a plastic, such as polyactide (PLA), co-polyesters, acrylonitrile butadiene styrene (ABS), polyethylene (PE), Nylon, polyurethane (PU), and the like. The plastic may be layered in such a way that the filter media 34 defines a plurality of pores, as further described below.

The tracer material 56 may be a chemical tracer that can be detected in the fluid (e.g., oil) to determine information about the interaction of the fluid with the filter, such as flow rate through the filter, pressure through the filter, and amount of time the filter element 14 has been used. For example, the tracer material 56 may include chromophores or organometallics of heavy elements including zirconium, cerium, yttrium, scandium, lanthanum, and the like. The tracer material 56 may be configured to dissolve or diffuse into the fluid (e.g., oil) as the fluid is passed through the filter element 14 to provide an indication of the amount of fluid that has passed through the filter element 14, as described below. For example, the tracer material 56 may react and activate at certain temperatures that cause the tracer material 56 to diffuse into the fluid passing through the filter element 14. The tracer material 56 may be embedded, encased, attached, absorbed, or otherwise coupled to or within the filtering material 54. The filter element 14 may contain an amount of tracer material 56 such that the tracer material 56 may constitute at least 3-20 parts per million (ppm) of the fluid after the tracer material 56 has dissolved from the filter element 14. However, any amount of tracer material 56 may be used such that the tracer material 56 may dissolve or diffuse from the filtering material 54 into the fluid being passed through the filter element 14 without significantly altering the structure of filter element 14 or affecting the fluid being filtered.

Figure 3:
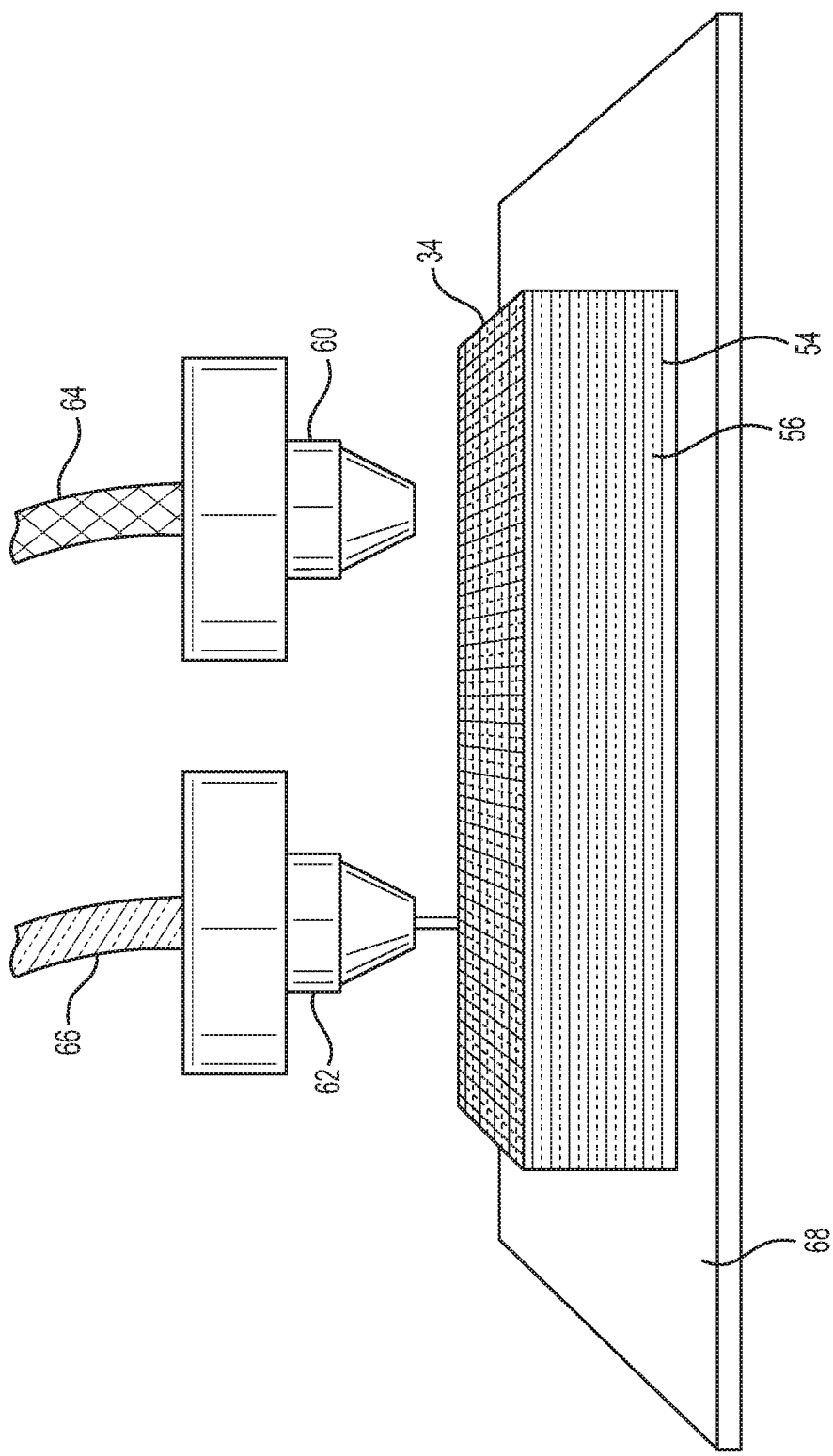
FIG. 3 illustrates a filter media of the filter element of FIGS. 2A and 2B manufactured by an additive manufacturing process.

FIG. 3 illustrates a perspective view of the filter media 34 manufactured by an additive manufacturing process. As shown in FIG. 3, the filter media 34 may be manufactured by a 3D printing process, such as fused filament fabrication (FFF), fused deposition modeling (FDM), stereolithography (SLA), or the like. However, filter media 34 may be manufactured using other conventional techniques such as, for example, casting or molding, and the like. The 3D printing process of the present disclosure may include a printing head having a first nozzle 60 and a second nozzle 62. The first nozzle 60 may dispense a standard filament 64 of filtering material 54, such as plastic. The second nozzle 62 may dispense tracer filament 66 of tracer material 56, such as at least one of chromophores, organometallics such as zirconium, cerium, yttrium, scandium, and lanthanum, or other heavy elements. In one embodiment, the tracer filament 66 may include only tracer material 56. In other embodiments, the tracer material and the filtering material may be joined to make a combined filament 66 to be dispensed from a nozzle 62. For example, tracer material 56 may be premixed with filtering material 54 before being fed through second nozzle 62.

A method of manufacturing a filter media 34 by an additive manufacturing process may include a step of depositing a first layer of filtering material 54 onto a bed 68. A second layer of filtering material 54 premixed with tracer material 56 may then be deposited onto the first layer of filtering material 54. A third layer of filtering material 54 may be deposited onto the second layer of filtering material 54 premixed with tracer material 56. This pattern may be repeated until the filter media 34 is fully constructed. Any number of layers of filtering material 54 may be deposited before a layer of filtering material 54 premixed with tracer material 56 is deposited. For example, a layer of filtering material 54 premixed with tracer material 56 may be deposited for every n-number of layers of filtering material 54. Further, the tracer material 56 may be dispensed in such a way as to create a geometry of a brand or other type of identification on the housing 12 and/or the filter element 14. For example, when the tracer material 56 is made of chromophores, an Ultra Violet (UV) light may be used to light up and/or make the chromophores visible to identify the branding or other identification.

In one embodiment, a method of manufacturing the filter media 34 may include a step of providing a computer-readable three-dimensional model of the filter media 34. The three-dimensional model may be configured to be converted into a plurality of slices that each define a cross-sectional layer of the filter media 34. Each layer of the filter media 34 may be successively formed by additive manufacturing, as described above. Additionally, the additive manufacturing process may include building a plurality of layers. The plurality of layers may include at least one first layer of filtering material 54 and at least one second layer of permeable 54 premixed with tracer material 56. Any number and pattern of first layers of filtering material 54 and second layers of filtering material 54 premixed with tracer material 56 may be used, such that the plurality of layers constitute a complete structure of the filter media 34.

Filter media 34' may be manufactured using an additive manufacturing process, similar to the process described above with respect to filter media 34. A method of manufacturing a filter media 34' by an additive manufacturing process may include a step of depositing a plurality of layers of filtering material 54 onto a bed 68. Tracer material 56 may be deposited between layers of filtering material 54 to form tracer element 58 such that tracer element 58 is located within filter media 34'. Tracer material 56 may be deposited in any shape and/or size between layers of filtering material 54. Additionally, tracer material 56 may be deposited to form any number of tracer elements 58 within filter media 34'.

The method of manufacturing filter media 34 and filter media 34' may utilize existing additive manufacturing technologies to produce a repeatable process that may generate a porous filter media 34 or filter media 34' of a useable efficiency grade. The process may include 3D printing hardware, and specific control of the movement patterns of the printing head (e.g., the first nozzle 60 and the second nozzle 62) so that as the material is added to the part, small gaps may be created to build a porous structure. Additionally, the method may utilize an open source software that generates the filter media 34 or filter media 34' based on inputs given to it by a user. The method may vary the speed and path of the printing head, the flow rate of the plastic being deposited, cooling methods, etc. The structure that is laid down may droop or otherwise deform so that small sized pores may be created. For example, the material may drip from one layer to the next layer, creating a seal with the next layer, thus creating two (or more) pores and finer porosity in the filter media 34 or filter media 34'. Deformation (e.g., dripping, drooping, etc.) may occur from the heat retained in the hot nozzle in the newest created layer and gravity. As a result, the previous laid layer may be attached to the new layer. The desired deformation may include adjusting the temperature control, control of layer height, extrusion width, infill pattern, etc.

The additive manufacturing process described above may also be used to manufacture all or some of the other components of oil filter 10, such as housing 12. For example, housing 12 may be manufactured by the 3D printing process using the same or different material than the filter element 14. Further, housing 12 may be formed to contain the tracer material 56. In other embodiments, tracer material 56 may be located in a plurality of components of oil filter 10. For example, tracer material 56 may be located in filter element 14, top portion 38 or bottom portion 40 of housing 12, or otherwise located within surfaces that may be in contact with the fluid as the fluid is passed through oil filter 10.

INDUSTRIAL APPLICABILITY

The disclosed aspects of oil filter 10 may be used in any machine that includes a fluid system that includes one or more filter elements. Filter element 14 described herein may provide for a number of commercial and manufacturer benefits including determining information about the filter element 14, the filtered fluid, and/or the housing 12 of the oil filter 10. For example, the amount of tracer material 56 that has dissolved into the fluid (e.g., oil) may be used to determine the need to replace a filter, the frequency that the oil has been changed, and/or if a specific oil filter 10 or filter element 14 has been used.

As described above, tracer material 56 may dissolve, or otherwise diffuse, into the fluid as the fluid is passed through the filter element 14. The tracer material 56 may include a material, such as chromophores or organometallics such as zirconium, cerium, yttrium, scandium, lanthanum and the like, such that the amount of tracer material 56 in the fluid may readily and easily be discernible. The amount of tracer material 56 in the fluid could be measured by fluorescence, Ultra Violet (UV) absorption and/or a chemical tracer testing tool or otherwise analyzing the oil saturated with tracer material 56 by analytical methods such as fluorescence absorption, conductivity, refractive index, elemental spectrometry, and the like. The tracer material 56 may help in determining information about the filter element 14 and/or housing 12. Information, such as length of time of filter use, flow rate through the filter, and pressure through the filter may be determined based on empirical data of the rate of dissolution of tracer material 56 under various conditions. Mixing the tracer material 56 with the filtering material 54 or locating the tracer element 58 of tracer material 56 within the filtering material 54 of the filter element 14 may also allow a user to determine the amount of wear of the filter element 14. For example, as the filtering material 54 erodes due to the flow of the fluid through filter element 14, the tracer material 56 may dissolve, or be released, into the fluid. The amount of tracer material 56 deposited within the filtering material 54 may be known, such that the amount of tracer material 56 that has dissolved into the fluid may correspond to the amount of wear of the filter element 14.

Filter element 14 with tracer material 56 may also be used to confirm usage of a specific oil filter 10 or filter element 14 for a specific machine or operation. For example, the tracer material 56 may identify the origin or manufacturer of the filter element 14. Such information may be used to help confirm that the appropriate filter element 14 is being used in a particular system. Additionally, filter element 14 of the present disclosure may be used to confirm proper use and replacement of the filter element 14. The amount of tracer material 56 in the oil may confirm or challenge whether an appropriate use and service of the filter element 14 maintained for the system. The amount of tracer material 56 in the oil may also determine the length of time the oil filter 10 was being used or if the oil filter 10 was changed frequently enough.

The disclosed filter media 34 may be manufactured using conventional techniques such as, for example, casting or molding. Alternatively, the disclosed filter media 34 may be manufactured using techniques generally referred to as additive manufacturing or additive fabrication. Additive manufacturing/fabrication processes include techniques such as, for example, 3D printing. 3D printing is a process wherein material may be deposited in successive layers under the control of a computer. The computer controls additive fabrication equipment to deposit the successive layers according to a three-dimensional model (e.g. a digital file such as an AMF or STL file) that is configured to be converted into a plurality of slices, for example substantially two-dimensional slices, that each define a cross-sectional layer of the filter media 34 in order to manufacture, or fabricate, the filter media 34. In one case, the disclosed filter media 34 would be an original component and the 3D printing process would be utilized to manufacture the filter media 34. In other cases, the 3D process could be used to replicate an existing filter media 34 and the replicated filter media 34 could be sold as aftermarket parts. These replicated aftermarket filter media 34 could be either exact copies of the original filter element or pseudo copies differing in only non-critical aspects.

Figure 4:
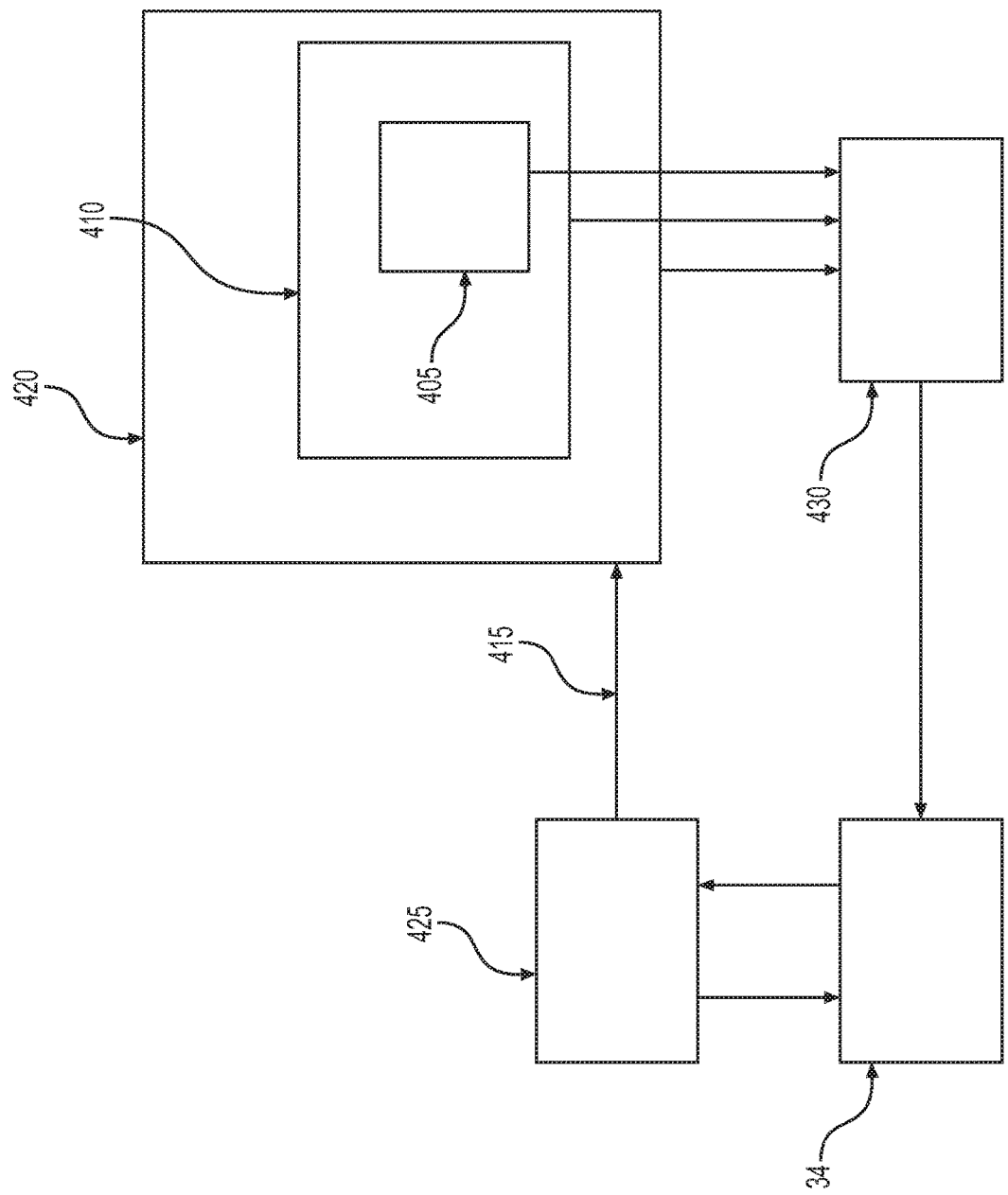
FIG. 4 illustrates a schematic drawing representing a system for generating the filter media of FIG. 3 by the additive manufacturing process.

With reference to FIG. 4, the three-dimensional model used to represent an original filter media 34 may be on a computer-readable storage medium 410 such as, for example, magnetic storage including floppy disk, hard disk, or magnetic tape; semiconductor storage such as solid state disk (SSD) or flash memory; optical disc storage; magneto-optical disc storage; or any other type of physical memory on which information or data readable by at least one processor may be stored. This storage medium may be used in connection with commercially available 3D printers 430 to manufacture, or fabricate, the filter media 34. Alternatively, the three-dimensional model may be transmitted electronically to the 3D printer 430 in a streaming fashion without being permanently stored at the location of the 3D printer 430. In either case, the three-dimensional model constitutes a digital representation of the filter media 34 suitable for use in manufacturing the filter media 34.

The three-dimensional model may be formed in a number of ways. In general, the three-dimensional model is created by inputting data 415 representing the filter media 34 to a computer or a processor 420 such as a cloud-based software operating system. The data may then be used as a three-dimensional model representing the physical filter media 34. The three-dimensional model is intended to be suitable for the purposes of manufacturing the filter media 34. In an exemplary embodiment, the three-dimensional model is suitable for the purpose of manufacturing the filter media 34 by an additive manufacturing technique.

In one embodiment depicted in FIG. 4, the inputting of data may be achieved with a 3D scanner 425. The method may involve contacting the filter media 34 via a contacting and data receiving device and receiving data from the contacting in order to generate the three-dimensional model. For example, 3D scanner 425 may be a contact-type scanner. The scanned data may be imported into a 3D modeling software program to prepare a digital data set. In one embodiment, the contacting may occur via direct physical contact using a coordinate measuring machine that measures the physical structure of the filter media 34 by contacting a probe with the surfaces of the filter media 34 in order to generate a three-dimensional model. In other embodiments, the 3D scanner 425 may be a non-contact type scanner and the method may include directing projected energy (e.g. light or ultrasonic) onto the filter media 34 to be replicated and receiving the reflected energy. From this reflected energy, a computer would generate a computer-readable three-dimensional model for use in manufacturing the filter media 34. In various embodiments, multiple 2D images can be used to create a three-dimensional model. For example, 2D slices of a 3D object can be combined to create the three-dimensional model. In lieu of a 3D scanner, the inputting of data may be done using computer-aided design (CAD) software. In this case, the three-dimensional model may be formed by generating a virtual 3D model of the disclosed filter media 34 using the CAD software. A three-dimensional model would be generated from the CAD virtual 3D model in order to manufacture the filter media 34.

The additive manufacturing process utilized to create the disclosed filter media 34 may involve materials such as plastic, rubber, metal, etc. In some embodiments, additional processes may be performed to create a finished product. Such additional processes may include, for example, one or more of cleaning, hardening, heat treatment, material removal, and polishing. Other processes necessary to complete a finished product may be performed in addition to or in lieu of these identified processes.

The additive manufacturing process described above may also be used to manufacture all or some of the components of oil filter 10, such as housing 12 and filter element 14. For example, housing 12 and filter element 14 may be manufactured by the 3D printing process using the same or different material than the filter media 34.

It will be apparent to those skilled in the art that various modifications and variations can be made to the disclosed system without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims and their equivalents.

What is claimed is:

1. An oil filter, comprising:
    an inlet;
    an outlet; and
    a filter element located downstream of the inlet and upstream of the outlet, the filter element including:
        one or more first layers having a filtering material without tracer material; and
        one or more second layers having combined filtering material with a filament comprising a tracer material including a chromophore within the filtering material.

2. The oil filter of claim 1, wherein the tracer material is configured to dissolve or diffuse into the oil as the oil is passed through the filter element to provide an indication of the amount of oil that has passed through the filter element.

3. The oil filter of claim 2, wherein the tracer material reacts and activates at certain temperatures to diffuse into the oil.

4. The oil filter of claim 1, wherein the filament comprising tracer material is disposed within and located throughout the one or more second layers.

5. The oil filter of claim 1, wherein the tracer material is formed as a solid structure located within the filtering material.

6. The oil filter of claim 1, wherein the filtering material is formed by an additive manufacturing process, and
    wherein the tracer material is added to the filter element by the additive manufacturing process.

7. The oil filter of claim 6, wherein the tracer material is added to the filter element in such a way as to create a geometry of a brand or other type of identification on the filter element.

8. The oil filter of claim 1, wherein the one or more first layers include a filament of filtering material without tracer material, and wherein the filament in the one or more second layers include of combined filtering material and tracer material within the filament.

9. The oil filter of claim 8, wherein the filter element comprises a porous structure including the one or more first layers and the one or more second layers.

10. A filter element for a liquid filter, comprising:
    one or more first layers having a filtering material without tracer material; and
    one or more second layers having combined filtering material with a filament comprising a tracer material including a chromophore within the filtering material.

11. The filter element of claim 10, wherein the one or more first layers include a filament of filtering material without tracer material, and wherein the filament in the one or more second layers include combined filtering material and tracer material within the filament.

12. The filter element of claim 10, wherein the tracer material is configured to dissolve into the liquid as the liquid is passed through the filter element to provide an indication of the amount of liquid that has passed through the filter element.

13. The filter element of claim 12, wherein the tracer material reacts and activates at certain temperatures to diffuse into the liquid.

14. The filter element of claim 10, wherein the filament comprising tracer material is disposed within and located throughout the one or more second layers.

15. The filter element of claim 10, wherein the tracer material is formed as a solid structure located within the filtering material.

16. The filter element of claim 10, wherein the filter element includes at least 3 parts per million (ppm) of tracer material.

17. The filter element of claim 10, wherein the filtering material is formed by an additive manufacturing process, and
    wherein the tracer material is added to the filter element by the additive manufacturing process.

18. The filter element of claim 17, wherein the tracer material is premixed with the filtering material to form the filament.

19. A liquid filter, comprising:
    a filter element including:
        a filtering material formed by an additive manufacturing process and configured to allow liquid to pass through the filter element such that contaminants are removed from the liquid; and
        a tracer material including a chromophore added to the filter element by the additive manufacturing process, the tracer material configured to dissolve into the liquid as the liquid passes through the filter element to provide an indication of the amount of liquid that has passed through the filter element, wherein the additive manufacturing process comprises:
        depositing one or more first layers of a filtering material without tracer material;
        depositing one or more second layers of combined filtering material with a filament comprising the tracer material within the filtering material onto the first layer; and
        depositing one or more third layers of the filtering material without tracer material onto the second layer.

20. The liquid filter of claim 19, wherein the one or more first layers and the one or more third layers include a filament of filtering material without tracer material, and wherein the filament in the one or more second layers include combined filtering material and tracer material within the filament.

* * * * *